United States Patent [19]

Merger et al.

[11] 4,328,354
[45] May 4, 1982

[54] PREPARATION OF METHYLENE-BIS-PHENYLCARBAMIC ACID ESTERS AND POLYMETHYLENE-POLYPHENYLCARBAMIC ACID ESTERS

[75] Inventors: Franz Merger, Frankenthal; Gerhard Nestler, Ludwigshafen, both of Fed. Rep. of Germany

[73] Assignee: BASF Aktiengesellschaft, Fed. Rep. of Germany

[21] Appl. No.: 248,982

[22] Filed: Mar. 30, 1981

[30] Foreign Application Priority Data

Apr. 11, 1980 [DE] Fed. Rep. of Germany ....... 3013907

[51] Int. Cl.³ .......................................... C07C 125/07
[52] U.S. Cl. ..................................................... 560/25
[58] Field of Search ........................................ 560/25

[56] References Cited

U.S. PATENT DOCUMENTS

| | | | |
|---|---|---|---|
| 2,946,768 | 7/1960 | Klauke et al. | 560/25 |
| 4,146,727 | 3/1979 | Shawl et al. | 560/25 |
| 4,162,362 | 7/1979 | Shawl | 560/25 |
| 4,163,019 | 7/1979 | Mango | 560/25 |
| 4,230,877 | 10/1980 | Shawl et al. | 560/25 |
| 4,243,815 | 1/1981 | Merger et al. | 560/25 |

*Primary Examiner*—G. T. Breitenstein
*Attorney, Agent, or Firm*—Keil & Witherspoon

[57] ABSTRACT

Methylene-bis-phenylcarbamic acid esters and polymethylene-polyphenylcarbamic acid esters are prepared by reacting N-phenylcarbamic acid esters with formaldehyde, formaldehyde derivatives or formaldehyde donors in the presence of carboxylic acids having a $pK_a$ of less than 4.

3 Claims, No Drawings

PREPARATION OF METHYLENE-BIS-PHENYLCARBAMIC ACID ESTERS AND POLYMETHYLENE-POLYPHENYLCARBAMIC ACID ESTERS

The present invention relates to a novel process for the preparation of methylene-bis-phenylcarbamic acid esters and higher homologous polymethylene-polyphenylcarbamic acid esters derived therefrom by reacting an N-phenylcarbamic acid ester with formaldehyde or a formaldehyde donor in the presence of a carboxylic acid.

Methylene-bis-phenylcarbamic acid esters and higher homologs derived therefrom are valuable starting materials for the preparation of methylene-bis-phenyl isocyanates and the corresponding polymethylene-polyphenyl isocyanates, which are known to be useful for the preparation of polyurethanes (German Laid-Open Application DOS No. 2,635,490). The commercially available isosyanates of this type are in general prepared by phosgenating the amines obtained on condensing aniline with formaldehyde in the presence of an aqueous acid.

The methylene-bis-phenylcarbamic acid esters are prepared by reacting such aniline/formaldehyde condensates with chloroformic acid esters in the presence of a base, or by reacting the corresponding isocyanates with alcohols.

These processes have the disadvantage that reaction with phosgene, a strongly toxic compound, requires an expensive technology, for safety reasons, and that the removal of the acids which are either required, or formed as by-products, in the various reactions entails severe pollution of the environment.

Methylene-bis-phenylcarbamic acid esters can also be prepared by reacting methylene-bis-nitrophenyl with an alcohol and carbon monoxide (cf. German Published Application DAS No. 1,568,044). Since the preparation of the nitro compounds required is very difficult, this process has not acquired any industrial importance.

U.S. Pat. No. 2,946,768 describes a process in which a phenylcarbamic acid ester is heated with formaldehyde or a formaldehyde donor in the presence of an acid. It states that the condensates obtained contain C-C bonds, but the presence of N-C bonds is not ruled out (cf. column 2, lines 65-70).

German Laid-Open Applications DOS No. 2,832,379 states that using analytical methods not known at the earlier date, it has been possible to prove that in the process of U.S. Pat. No. 2,946,768 formaldehyde tends to react at the nitrogen of the carbamic acid ester and that therefore 15-50% by weight of undesired products with N-C bonds are formed. This result is confirmed by a comparative example (cf. Example 1) carried out analogously to Example 2 of U.S. Pat. No. 2,946,768. Furthermore, other by-products are also formed; for example, acid hydrolysis of the carbamic acid ester results in amines (cf. German Laid-Open Application DOS No. 2,832,379, page 3).

Since there is no process for separating off the nitrogen-linked products, which do not give isocvanates on pyrolysis, the reaction mixtures prepared according to U.S. Pat. No. 2,946,768 are unsuitable for the preparation of isocyanates. Accordingly, the said process is technically and economically unsatisfactory.

German Laid-Open Application DOS No. 2,832,379 describes a process for the rearrangement of these undesired by-products to give methylene-bis-phenylcarbamic acid esters and the higher homologous polymethylene-polyphenylcarbamic acid esters derived therefrom. In this process, the reaction mixtures prepared by the process of U.S. Pat. No. 2,946,768 are reacted with strong protonic acids or Lewis acids under virtually anhydrous conditions at 50°-170° C.

The disadvantage of this technically difficult and two-stage process is that first a condensate must be prepared, by the process of U.S. Pat. No. 2,946,768, from a phenylcarbamic acid ester and formaldehyde in the presence of a substantial amount of an aqueous acid, then the product has to be freed from the acid and dried, and finally it must be again reacted, this time under anhydrous conditions, with a large amount of acid, which at the end of the reaction again has to be removed completely. The pollution of the effluent by the large amounts of acid and the by-products which are to some extent formed, for example by the amines formed during acid hydrolysis, is a serious problem.

U.S. Pat. No. 4,162,362 describes the one-step condensation of ethyl phenylcarbamate with formaldehyde or a formaldehyde donor in the presence of a sulfonic acid. This requires relatively large amounts of sulfonic acid, based on carbamic acid ester. Since the reaction product must be washed acid-free it is necessary, in view of the high viscosity of the condensate, to employ a solvent and an expensive working-up process. The pollution of the environment resulting from the disposal of the sulfonic acid is considerable.

We have found that in the preparation of methylene-bis-phenylcarbamic acid esters and polymethylene-polyphenylcarbamic acid esters reacting an N-phenylcarbamic acid ester with formaldehyde, a formaldehyde derivative or a formaldehyde donor, the above disadvantages may be avoided if the reaction is carried out in the presence of a carboxylic acid having a $pK_a$ of less than 4.

In contrast to the above conventional processes, in which the removal of the acid used entails an involved and expensive procedure which also pollutes the environment, the carboxylic acid used in the process according to the invention can simply be removed by distillation. Accordingly, recycling the carboxylic acid to the process is an extremely simple matter.

In the case of the formation of the methylene-bis-(4-phenylcarbamic acid ester) from methyl N-phenylcarbamate and formaldehyde, the reaction can be represented by the following equation.

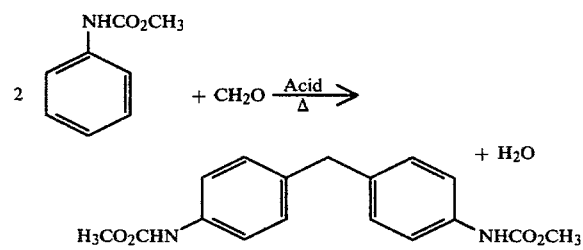

The process according to the invention at the same time forms higher homologous polymethylene-polyphenylcarbamic acid esters, ie. carbamic acid esters containing 3 or more benzene rings linked by methylene bridges, since, to a lesser degree, formaldehyde also reacts with methylene-bis-phenylcarbamic acid ester already formed.

Examples of suitable N-phenylcarbamic acid esters are compounds of the formula

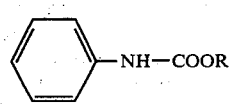

where R is alkyl of 1 to 3 carbon atoms and phenyl may be substituted in the o- and/or m-position, for example by methyl or methoxy or by halogen, eg. chlorine or bromine.

Examples of suitable N-phenylcarbamic acid esters are methyl, ethyl and propyl N-phenylcarbamate, methyl and ethyl N-o-tolylcarbamate, methyl N-2,6-dimethylphenylcarbamate and ethyl N-o-chlorophenylcarbamate.

Instead of formaldehyde, a formaldehyde donor, such as paraformaldehyde or trioxane, or certain specific formaldehyde derivatives, can be used. Examples of the last-mentioned are compounds of the general formula $X-CH_2-X$, where X is OR, SR or OCOR, and R is alkyl, preferably of 1 to 3 carbon atoms. Where acetals are used, they are preferably those in which the alkyl radical corresponds to the alkanol on which the carbamic acid ester is based. Dimethylformal is particularly advantageous, since it can be prepared very easily and economically from aqueous formaldehyde and methanol.

The reaction according to the invention is in general carried out at up to 160° C., preferably at 30°–160° C., especially at 40°–140° C.

The molar ratio of formaldehyde:carbamic acid ester is advantageously from 1:0.5 to 1:10, preferably from 1:1.5 to 1:3. If, however, it is mainly the methylene-bis-phenylcarbamic acid ester which is to be prepared, a ratio of from 1:4 to 1:8 is preferred.

Examples of suitable carboxylic acids with $pK_a$'s of less than 4, which are used, for instance, in amounts of from 1 to 300, preferably from 10 to 200, % by weight, based on carbamic acid ester, are formic acid, dichloroacetic acid, trichloroacetic acid, trifluoroacetic acid, oxalic acid or mixtures of these acids. The reaction, which is complete after about 1–20 hours, is in general carried out by either slowly adding formaldehyde or the corresponding compound to a stirred mixture of the carbamic acid ester and the acid, at the reaction temperature, or by heating a stirred mixture of the carbamic acid ester, the formaldehyde component and the acid and keeping it at the reaction temperature for the appropriate time. At times it is also advantageous to start the reaction at a lower temperature and then to raise the temperature stepwise. The reaction product is isolated by conventional methods, for example by distilling off the carboxylic acid, any solvent present, and unconverted starting material.

The condensation can be carried out in the absence or presence of a solvent, such as benzene, methylcyclohexane, acetic acid, methanol, methyl acetate, nitrobenzene, chlorobenzene, dichlorobenzene or an aliphatic chlorohydrocarbon. If a solvent is necessary, it is however preferred to let the carboxylic acid, employed as the catalyst, serve as the solvent.

The reaction can be carried out under atmospheric or superatmospheric pressure.

EXAMPLE 1 (COMPARATIVE EXAMPLE)

Using a method similar to Example 2 of German Pat. No. 1,042,891, a stirred mixture of 183 parts of methyl phenylcarbamate, 500 ml of water and 86 parts of 30% strength aqueous formaldehyde solution is heated to 100° C., and 100 ml of concentrated hydrochloric acid are then added. Thereafter the reaction mixture is stirred for 20 hours at 100° C. After completion of the reaction, the aqueous phase is separated off and the reaction product is washed three times with hot water. Unconverted starting material is then distilled off under reduced pressure. The residue is analyzed by means of high pressure liquid chromatography (HPLC). It contains 50% of methyl methylene-bis-phenylcarbamate, 9% of a trinuclear product, 16% of an N-C-bonded bi-nuclear product and 10% of an N-C-bonded trinuclear product. The remainder consists of polynuclear compounds not identified in more detail.

EXAMPLE 2

A mixture of 151 parts of methyl phenylcarbamate, 15 parts of trioxane and 200 parts of formic acid is heated to 100° C. in a stirred reactor, and stirring is continued at this temperature for 20 hours. After completion of the reaction, the mixture is subjected to distillation under reduced pressure. 145 parts of a distillation residue are obtained, consisting, according HPLC analysis, of 65% of methyl methylene-bis-phenylcarbamate, 22% of trinuclear product and 13% of polynuclear products.

EXAMPLE 3

A mixture of 151 parts of methyl phenylcarbamate, 66 parts of diacetoxymethane and 50 parts of oxalic acid is heated to 110° C. in a stirred reactor, and stirring is continued at this temperature for 20 hours. After completion of the reaction, unconverted starting material is distilled off under reduced pressure. 124 parts of a distillation residue are obtained, consisting, according to HPLC analysis, of 68% of methyl methylene-bis-phenylcarbamate, 17% of trinuclear product and 25% of polynuclear products.

EXAMPLE 4

A mixture of 151 parts of methyl phenylcarbamate, 50 parts of 60% strength aqueous formaldehyde solution and 300 parts of formic acid is heated to 100° C. in a stirred reactor, and stirring is continued at this temperature for 20 hours. After completion of the reaction, the mixture is subjected to distillation under reduced pressure. 138 parts of a distillation residue are obtained, consisting, according to HPLC analysis, of 58% of methyl methylene-bis-phenylcarbamate, 22% of trinuclear product and 20% of polynuclear products.

EXAMPLE 5

A mixture of 151 parts of methyl phenylcarbamate, 15 parts of paraformaldehyde and 200 parts of trifluoroacetic acid is heated to 100° C. in a stirred reactor and stirring is continued at this temperature for 20 hours. After completion of the reaction, the acid and unconverted starting material are distilled off under reduced pressure. 130 parts of a distillation residue are obtained, consisting, according to HPLC analysis, of 51% of methyl methylene-bis-phenylcarbamate, 19% of trinuclear product and 30% of polynuclear products.

We claim:

1. A process for the preparation of methylene-bis-phenylcarbamic acid esters and polymethylene-polyphenylcarbamic acid esters which comprises reacting an N-phenylcarbamic acid ester with formaldehyde, a formaldehyde derivative or a formaldehyde donor in the presence of a carboxylic acid having a $pK_a$ of less than 4.

2. The process of claim 1, wherein the reaction is carried out at from 30° to 160° C.

3. The process of claim 1 or 2, wherein the carboxylic acid having a $pK_a$ of less than 4 is formic acid, oxalic acid, dichloroacetic acid, trichloroacetic acid or trifluoroacetic acid.

* * * * *